(12) United States Patent
Tallinen et al.

(10) Patent No.: US 12,605,564 B2
(45) Date of Patent: Apr. 21, 2026

(54) RADIATION TREATMENT PLAN OPTIMIZATION EMPLOYING A MORPHED FLUENCE MAP

(71) Applicant: Siemens Healthineers International AG, Steinhausen (CH)

(72) Inventors: Tuomas Tallinen, Espoo (FI); Esa Kuusela, Espoo (FI); Shahab Basiri, Siuntio (FI)

(73) Assignee: Siemens Healthineers International AG, Steinhausen (CH)

( * ) Notice: Subject to any disclaimer, the term of this patent is extended or adjusted under 35 U.S.C. 154(b) by 323 days.

(21) Appl. No.: 18/192,952

(22) Filed: Mar. 30, 2023

(65) Prior Publication Data

US 2024/0325781 A1 Oct. 3, 2024

(51) Int. Cl.
*A61N 5/10* (2006.01)
*G16H 20/40* (2018.01)

(52) U.S. Cl.
CPC .......... *A61N 5/103* (2013.01); *A61N 5/1071* (2013.01); *G16H 20/40* (2018.01)

(58) Field of Classification Search
None
See application file for complete search history.

(56) References Cited

U.S. PATENT DOCUMENTS

| | | | |
|---|---|---|---|
| 7,266,175 B1 * | 9/2007 | Romesberg | A61N 5/103 378/65 |
| 2018/0272152 A1 * | 9/2018 | Kuusela | A61N 5/1031 |
| 2021/0244969 A1 | 8/2021 | Bokrantz | |
| 2022/0126117 A1 | 4/2022 | Voronenko | |
| 2023/0390585 A1 * | 12/2023 | Privalikhin | A61N 5/1048 |

OTHER PUBLICATIONS

Craft, David et al.; Multicriteria VMAT Optimization; Jan. 12, 2012 (Jan. 12, 2012), pp. 686-696, XP093173207, DOI: 10.1118/1.3675601] Retrieved from the Internet:URL:https://www.ncbi.nlm.nih.gov/pmc/articles/PMC3267794/pdf/MPHYA6-000039-000686_1.pdf.

(Continued)

*Primary Examiner* — Marcus H Taningco
(74) *Attorney, Agent, or Firm* — Fitch, Even, Tabin & Flannery LLP

(57) ABSTRACT

A control circuit calculates at least a first and a second fluence map corresponding to a given patient and then provides at least a third fluence map by morphing between the first and the second fluence map. Radiation treatment plan optimization can proceed as a function, at least in part, of those fluence maps. These teachings will accommodate initially subdividing a treatment arc corresponding to the radiation treatment plan into a plurality of dose calculation sectors. In such a case, the foregoing calculations can include calculating the first fluence map for a first one of the dose calculation sectors and calculating the second fluence map for a second one of the dose calculation sectors. By one approach, the first dose calculation sector does not overlap with the second dose calculation sector. By one approach, the first and second dose calculation sectors are adjacent to one another.

18 Claims, 3 Drawing Sheets

(56)     References Cited

OTHER PUBLICATIONS

Unkelbach, Jan et al.; Optimization approaches to volumetric modu-
lated arc therapy planning; Feb. 25, 2015 (Feb. 25, 2015), pp.
1367-1377, XP093173201, DOI: 10.1118/1.4908224] Retrieved from
the Internet:URL:https://www.ncbi.nlm.nih.gov/pmc/articles/
PMC5148175/pdf/MPHYA6-000042-001367_1.pdf.
Wala, Jeremiah et al.; Optimal partial-arcs in VMAT treatment
planning; Physics in Medicine and Biology, Institute of Physics
Publishing, Bristol GB, vol. 57, No. 18, Sep. 5, 2012 (Sep. 5, 2012),
pp. 5861-5874, XP020228269, ISSN: 0031-9155, DOI: 10.1088/
0031-9155/57/18/5861.
International Search Report and Written Opinion from related
International Application No. PCT/EP2024/058608 dated Jun. 21,
2024; 17 pages.

* cited by examiner

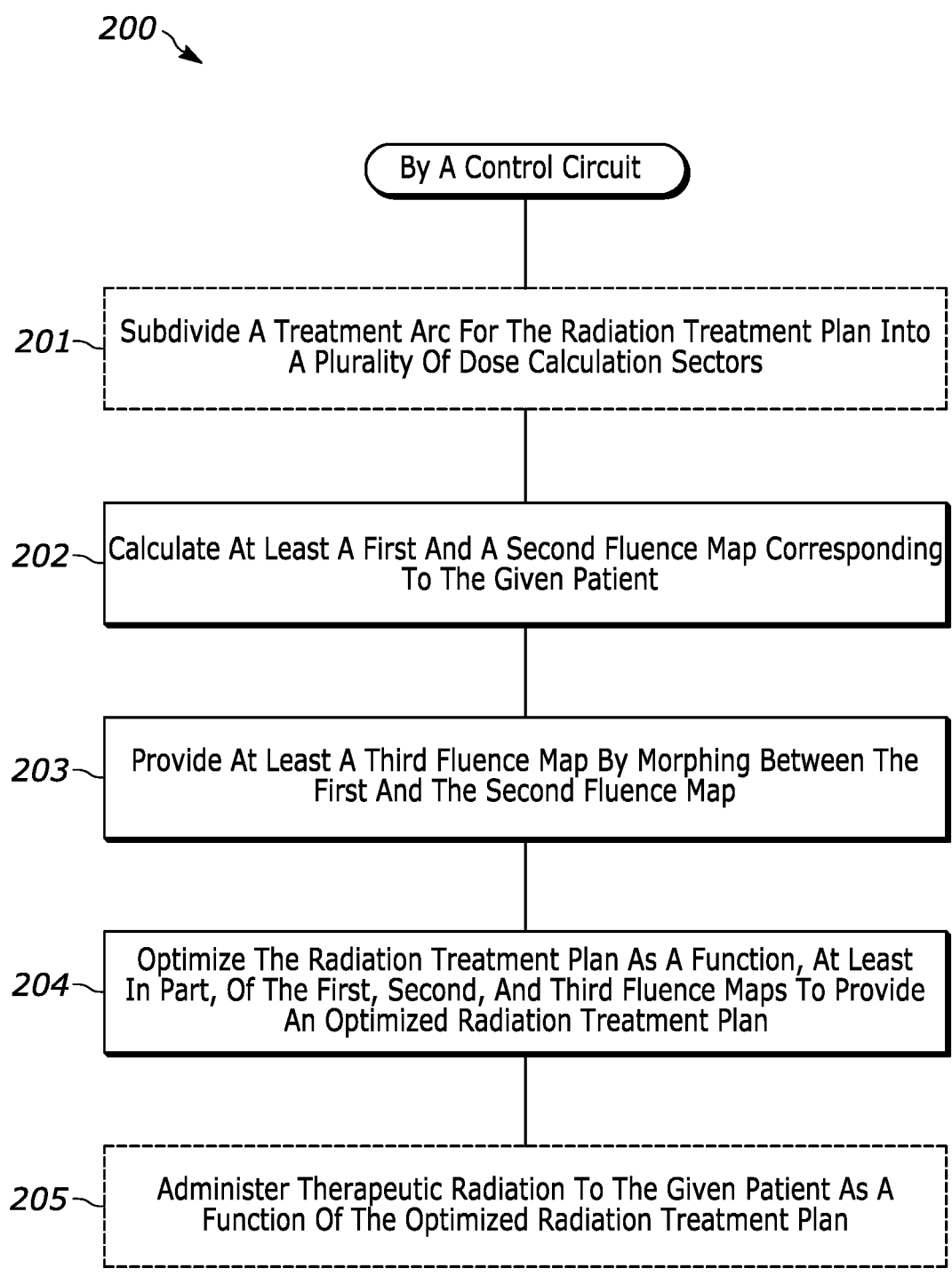

*200*

By A Control Circuit

*201* — Subdivide A Treatment Arc For The Radiation Treatment Plan Into A Plurality Of Dose Calculation Sectors

*202* — Calculate At Least A First And A Second Fluence Map Corresponding To The Given Patient

*203* — Provide At Least A Third Fluence Map By Morphing Between The First And The Second Fluence Map

*204* — Optimize The Radiation Treatment Plan As A Function, At Least In Part, Of The First, Second, And Third Fluence Maps To Provide An Optimized Radiation Treatment Plan

*205* — Administer Therapeutic Radiation To The Given Patient As A Function Of The Optimized Radiation Treatment Plan

FIG. 2

RADIATION TREATMENT PLAN OPTIMIZATION EMPLOYING A MORPHED FLUENCE MAP

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Many optimization approaches, such as volumetric modulated arc therapy optimization, require numerous dose calculations from a dense set of radiation beam directions. The latter activity unfortunately then typically increases computational loading and corresponding time frames. Depending upon a variety of factors, optimization in such cases can consume from tens of seconds to many minutes. To reduce such computational loading, some prior approaches employ simplified internal dose calculators that, for example, provide for course graining of dose calculation beam directions by grouping multiple control points into one dose calculation sector. While such an approach can reduce overall time requirements, such an approach also tends to offer reduced accuracy.

BRIEF DESCRIPTION OF THE DRAWINGS

The above needs are at least partially met through provision of the radiation treatment plan optimization employing a morphed fluence map apparatus and method described in the following detailed description, particularly when studied in conjunction with the drawings, wherein:

FIG. 2 comprises a flow diagram as configured in accordance with various embodiments of these teachings.

Figure 1:
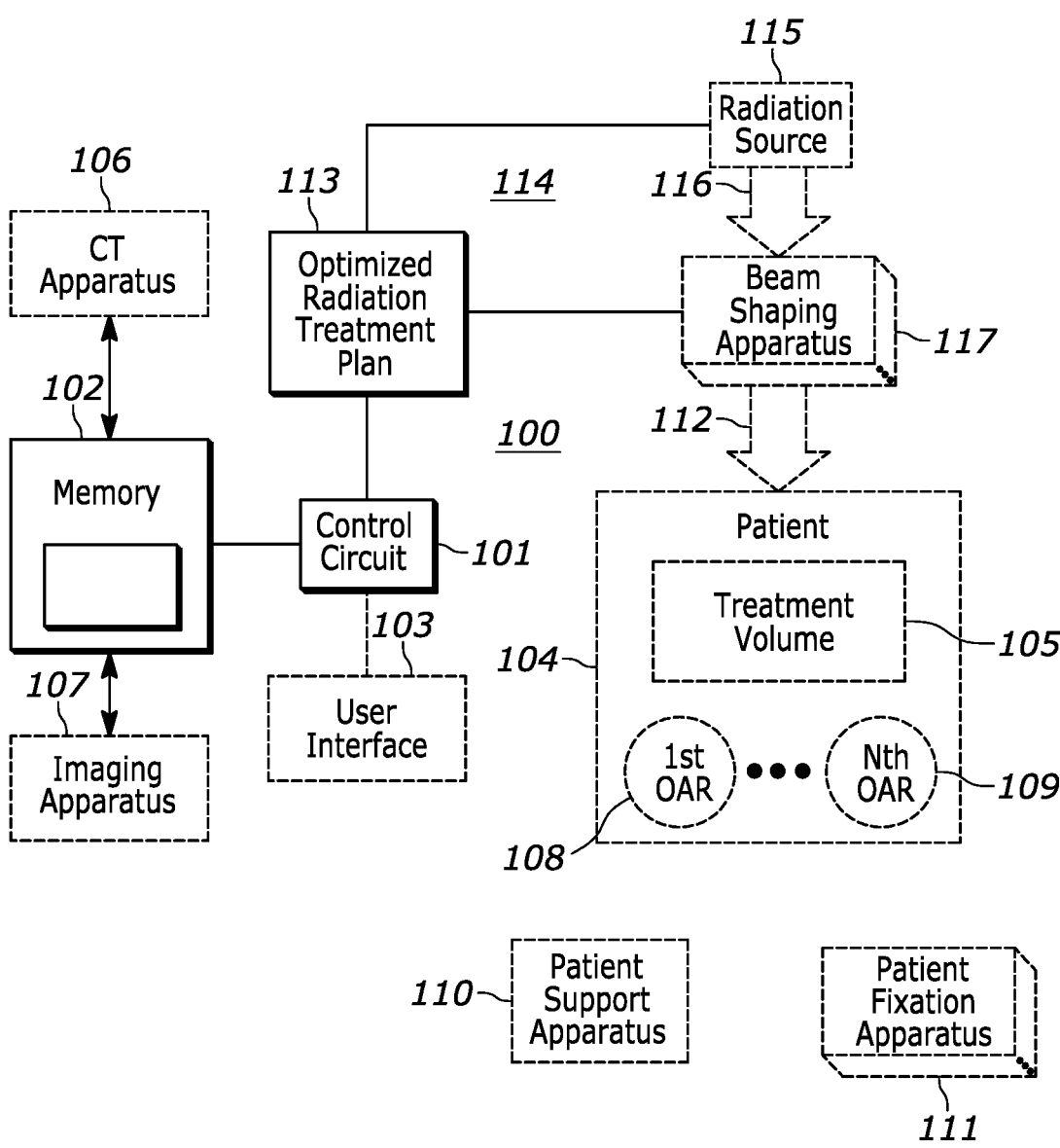
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, pursuant to these various embodiments, a control circuit calculates at least a first and a second fluence map corresponding to a given patient. The control circuit then provides at least a third fluence map by morphing between the first and the second fluence map. A radiation treatment plan can then be optimized as a function, at least in part, of the first, second, and third fluence maps to provide an optimized radiation treatment plan.

These teachings will accommodate initially subdividing a treatment arc corresponding to the radiation treatment plan into a plurality of dose calculation sectors. In such a case, the foregoing calculations can include calculating the aforementioned first fluence map for a first one of the plurality of dose calculation sectors and calculating the second fluence map for a second one of the plurality of dose calculation sectors. By one approach, the aforementioned first one of the plurality of dose calculation sectors does not overlap with the aforementioned second one of the plurality of dose calculation sectors. By one approach, the first and second dose calculation sectors are adjacent to one another.

By one approach, each of the aforementioned dose calculation sectors comprises a plurality of control points.

By one approach, each of the aforementioned first and second dose calculation sectors has only one corresponding calculated fluence map.

By one approach, these teachings will accommodate calculating a fluence map for each of the plurality of dose calculation sectors. By one approach, each such dose calculation sector has only a single corresponding calculated fluence map.

By one approach, each of the aforementioned calculated fluence maps are each centrally located with respect to its corresponding dose calculation sector.

So configured, the aforementioned third fluence map, formed by morphing at least two calculated fluence maps, can be used during optimization to predict fluence maps for beam directions that do not have a corresponding explicit dose calculation beam. As a result, optimization can be carried out with fewer actual dose calculation sectors or, alternatively, a same number of calculation sectors but with corresponding higher accuracy (for such results as leaf sequencing).

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient, information regarding a particular radiation treatment platform, fluence maps, and so forth, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction)

during an energy-based treatment session by the control circuit 101. As the foregoing elements and systems are well understood in the art, further elaboration in these regards is not provided here except where otherwise relevant to the description.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized radiation treatment plan 113 to thereby facilitate treating a particular patient with therapeutic radiation using a particular radiation treatment platform per that optimized radiation treatment plan.

At optional block 201, this process 200 will accommodate subdividing a treatment arc for a radiation treatment plan into a plurality of dose calculation sectors. Generally speaking, a treatment arc refers to the path that the source of a therapeutic radiation beam takes while delivering radiation to a patient during a radiation therapy session. In many application settings the radiation source will track a gantry that encircles (entirely or only partially) the patient. Accordingly, as one example, a treatment arc can comprise a 360 degree circle around the patient. A dose calculation sector, in turn, typically refers to a section of arc for which a dose of radiation is being calculated using a single beam direction centered in the sector. In particular, dose calculation sectors can be viewed as corresponding to various portions of the aforementioned treatment arc.

These teachings are highly flexible in practice and will accommodate a variety of approaches in the foregoing regards. The aforementioned treatment arc can be subdivided into essentially as many dose calculation sectors as one might wish. As one example, these teachings will accommodate subdiving a treatment arc into two, three, four, five, six, or more dose calculation sectors as desired.

It will be presumed here that each such dose calculation sector comprises a plurality of control points. The expression "control points" refers to the specific locations in a patient's treatment plan where the radiation beam is (or can be) turned on or off, and/or where the intensity of the readiation beam is (or can be) adjusted to ensure precise delivery of the prescribed radiation dose to the target area while minimizing exposure to healthy tissues.

For the sake of an illustrative example, let it be presumed that there are at least two dose calculation sectors for a given treatment arc. By one approach, these teachings will accommodate having a first such dose calculation sector and a second such dose calculation sector not overlap one another (though this first and second dose calculation sector may be adjacent to one another).

At block 202, the control circuit 101 calculates at least a first and a second fluence map corresponding to the given patient. In the foregoing illustrative example, the first fluence map is calculated for the first of the above-mentioned dose calculation sectors and the second fluence map is calculated for the second of the above-mentioned dose calculation sectors. Fluence represents radiative flux integrated over time and comprises a fundamental metric in dosimetry (i.e., the measurement and calculation of an absorbed dose of ionizing radiation in matter and tissue). By one approach, this activity serves to calculate only one fluence map per each dose calculation sector. In lieu of the foregoing, or in combination therewith, these teachings will also accommodate calculating and hence providing a fluence map to each of the aforementioned dose calculation sectors for the treatment arc.

A fluence map, in turn, refers to a graphical representation of the intensity of the radiation beam that will be delivered to a specific region of a patient's body. The fluence map provides a detailed plan of the radiation intensity that is needed to deliver a prescribed radiation dose to a target area while minimizing the exposure of healthy tissues. The calculation of fluence maps constitutes a known area of prior art endeavor that typically takes into account such things as a patient's anatomy, the location of the target area, and the desired radiation dose distribution. In a typical application setting, the calculations provide for dividing the radiation beam into a grid of small pixels or beamlets, and assigning a specific intensity value to each pixel or beamlet.

A fluence map can be displayed, for example, as a two-dimensional color-coded image, with different colors representing different intensities of radiation. The map provides a detailed visualization of the radiation intensity distribution across the target area, allowing radiation oncologists and medical technician/clinicians to carefully plan and optimize the radiation treatment plan.

As noted above, this activity may comprise calculating only one fluence map for each of the dose calculation sectors of the treatment arc. If desired, each such fluence map may be calculated, and hence correspond to, a central location of its corresponding dose calculation sector.

At block 203, this process 200 then provides for providing at least a third fluence map by morphing between the aforementioned first and second fluence maps. "Morphing" is often thought of as smoothly changing from one image to another through a series of small gradual steps using computer animation techniques. As used herein, "morphing" need not include creating a complete series of such maps. Instead, and as one example, a morphing-based fluence map can be created for a virtual beam direction of choice.

Figure 3:
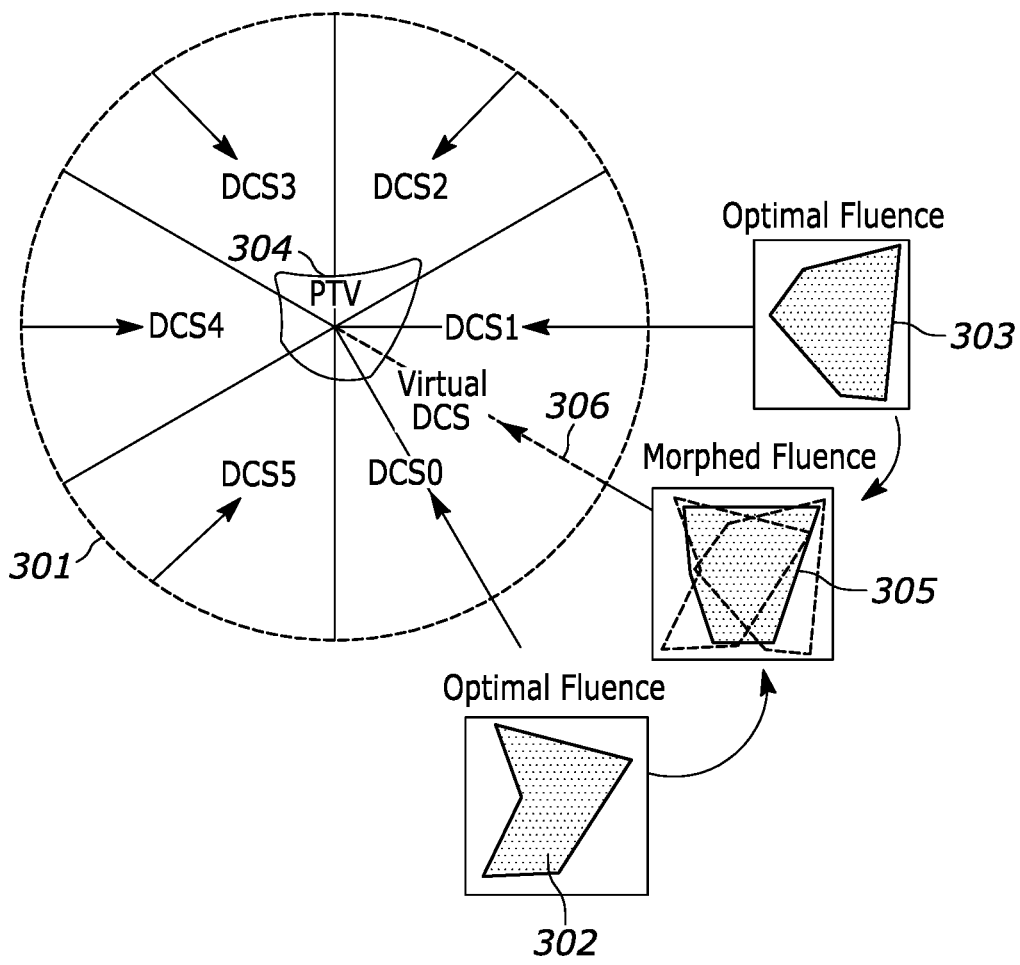
FIG. 3 comprises a schematic diagram as configured in accordance with various embodiments of these teachings.

FIG. 3 presents an illustrative example in the foregoing regards. In FIG. 3, a treatment arc 301 is subdivided into six equally-sized dose calculation sectors (denoted as DCS0 through DCS5). Each dose calculation sector has a corresponding beam direction that is represented by the solid arrows that point inwards towards the patient's treatment volume 304. In this example, each of these beam directions are centrally located with their respective dose calculation sector.

Pursuant to these teachings, a first fluence map 302 is then calculated for a first dose calculation sector DCS0 and a second fluence map 303 is calculated for a second dose calculation sector DCS1 (the latter, in this example, being directly adjacent to the first dose calculation sector DCS0). A third fluence map 305, which corresponds to a virtual beam direction denoted by reference numeral 306 that lies on on the boundary that separates the first and second dose calculation sectors, is then provided by morphing between the first fluence map 302 and the second fluence map 303 (in essence effecting a virtual dose calculation sector in the process). By using morphing techniques, this third fluence map 305 is produced without any three-dimensional dose volume calculations that would otherwise typify the calculation of such a map.

These teachings will accommodate any of a variety of approaches to accomplish the foregoing morphing. While these teachings presume an approach that is more than merely interpolating between the two fluence maps, by one approach, the morphing can comprise a combination of image warping and interpolation operations. Image warping, also known as image deformation, is a technique used to transform the shape of an image. This technique typically comprises mapping the pixels of an original image to new locations in an output image according to a mathematical function. There are various types of image warping techniques, including affine warping, projective warping, and non-linear warping. Affine warping involves transforming an image using a combination of scaling, rotation, and translation. Projective warping is similar to affine warping, but this approach allows for more complex transformations such as perspective distortion. Non-linear warping involves transforming an image using a more complex mathematical function, which can be used to create more dramatic changes in shape. Morphing may also use some additional geometric information about the treated volume, for example, warping can be aided by precomputed fluence plane masks of target volume.

As another illustrative example, these teachings will accommodate employing a properly trained machine learning model to predict the morphed third fluence map when the first and second fluence maps are provided as input (possibly along with other relevant information, such as the spacing between the relevant beam views).

These teachings will accommodate providing a virtual fluence map for any beam direction of choice along a treatment arc. If desired, and as one example, these teachings will support providing three morphed fluence maps that each correspond to virtual beam directions within a single dose calculation sector, while only providing one morphed fluence map for another, different dose calculation sector (or elsewhere one the treatment arc, such as on the boundary between two dose calculation sectors).

These teachings will also support a flexible approach to the creation of such morphed fluence maps. For example, these teachings will support providing all of the morphed fluence maps that have anticipated or potential use prior to using those maps in an optimization process. As another example, these teachings will support provided newly morphed (at the time of need) fluence maps based on calculated fluence maps that are calculated during the optimization process (for example, optimizing calculated fluence maps may include several three-dimensional dose calculations followed by calculations of an objective function and projections from a three-dimensional volume to the fluence plane).

At block 204, this process 200 then provides for optimizing a radiation treatment plan as a function, at least in part, of the aforementioned first, second, and third fluence maps to provide an optimized radiation treatment plan 113. Because morphed fluence maps can be generated far more quickly than fluence maps that are calculated in an ordinary manner, The overall process, including the optimization process, may have a considerably reduced time requirement that shaves many seconds or even many minutes off an otherwise expected timeframe. At the same time, efficacy and accuracy of the resultant optimized radiation treatment plan can equal, at least in many application settings, the results of a more traditional approach in these regards.

At optional block 205, this process 200 will provide for administering therapeutic radiation 112 to the given patient 104 as a function of the optimized radiation treatment plan 113 (using, for example, the above-described treatment platform 114).

So configured, these teachings can reduce the need for computational intense and expensive three-dimensional dose calculations and three-dimensional volume projections when optimizing Volumetric Modulated Arc Therapy radiation treatment plans and other modulated arc plans by replacing at least some previously-calculated fluence maps with morphed content that can be produced more quickly via faster two-dimensional processing on already-calculated fluence maps. As a result, these teachings make it possible to optimize dosimetrically high-quality radiation treatment plans in a reduced amount of time.

These teachings can be applied more generally to any fluence plane quantities. In the context of optimization, this includes, for example, fluence plane projections of derivatives of cost functions from dose volume. The fluence plane can also present a set of planes to present different fluences. For example, particles with different energies or qualities (such as, but not limited to, photons, electrons, and/or protons) might be presented with different fluence planes, and/or one can present the contribution of off-focal radiation by calculating fluence planes at different depths. (By one approach, when such multi-plane fluences are used in optimization, the morphing/warping can be applied to each of the fluence planes).

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to facilitate optimizing a radiation treatment plan for a given patient, the method comprising:
by a control circuit:
    calculating at least a first and a second fluence map corresponding to the given patient;
    providing at least a third fluence map by morphing between the first and the second fluence map;
    optimizing the radiation treatment plan as a function, at least in part, of the third fluence map to provide an optimized radiation treatment plan, wherein the third fluence map replaces at least a part of a previously-calculated fluence map;
by a radiation treatment platform:
    administering therapeutic radiation to the given patient as a function of the optimized radiation treatment plan.

2. The method of claim 1 further comprising:
subdividing a treatment arc for the radiation treatment plan into a plurality of dose calculation sectors;
and wherein calculating the at least a first and a second fluence map corresponding to the given patient comprises, at least in part, calculating the first fluence map for a first one of the plurality of dose calculation sectors and calculating the second fluence map for a second one of the plurality of dose calculation sectors.

3. The method of claim 2 wherein the first one of the plurality of dose calculation sectors does not overlap with the second one of the plurality of dose calculation sectors.

4. The method of claim 2 wherein the first one of the plurality of dose calculation sectors is adjacent to the second one of the plurality of dose calculation sectors.

5. The method of claim 2 wherein each of the first one of the plurality of dose calculation sectors and the second one of the plurality of dose calculation sectors only has one calculated fluence map.

6. The method of claim 2 wherein each of the dose calculation sectors has a corresponding calculated fluence map.

7. The method of claim 6 wherein each of the dose calculation sectors has only a single corresponding calculated fluence map.

8. The method of claim 7 wherein the calculated fluence map that corresponds to each of the dose calculation sectors is centrally located with respect thereto.

9. The method of claim 7 wherein each of the dose calculation sectors comprises a plurality of control points.

10. An apparatus to facilitate optimizing a radiation treatment plan for a given patient, the apparatus comprising:

a control circuit configured to:

calculate at least a first and a second fluence map corresponding to the given patient;

provide at least a third fluence map by morphing between the first and the second fluence map;

optimize the radiation treatment plan as a function, at least in part, of the third fluence map to provide an optimized radiation treatment plan, wherein the third fluence map replaces at least a part of a previously-calculated fluence map; and facilitate administering therapeutic radiation to the given patient as a function of the optimized radiation treatment plan via a radiation treatment platform.

11. The apparatus of claim 10 wherein the control circuit is further configured to:

subdivide a treatment arc for the radiation treatment plan into a plurality of dose calculation sectors;

and wherein the control circuit is further configured to calculate the at least a first and a second fluence map corresponding to the given patient by, at least in part, calculating the first fluence map for a first one of the plurality of dose calculation sectors and calculating the second fluence map for a second one of the plurality of dose calculation sectors.

12. The apparatus of claim 11 wherein the first one of the plurality of dose calculation sectors does not overlap with the second one of the plurality of dose calculation sectors.

13. The apparatus of claim 11 wherein the first one of the plurality of dose calculation sectors is adjacent to the second one of the plurality of dose calculation sectors.

14. The apparatus of claim 11 wherein each of the first one of the plurality of dose calculation sectors and the second one of the plurality of dose calculation sectors only has one calculated fluence map.

15. The apparatus of claim 11 wherein each of the dose calculation sectors has a corresponding calculated fluence map.

16. The apparatus of claim 15 wherein each of the dose calculation sectors has only a single corresponding calculated fluence map.

17. The apparatus of claim 16 wherein the calculated fluence map that corresponds to each of the dose calculation sectors is centrally located with respect thereto.

18. The apparatus of claim 16 wherein each of the dose calculation sectors comprises a plurality of control points.

\* \* \* \* \*